United States Patent
Beshay et al.

(10) Patent No.: US 10,557,857 B1
(45) Date of Patent: Feb. 11, 2020

(54) SYSTEM AND METHOD FOR BONE LOSS ASSAY

(71) Applicant: OPTECH VENTURES, LLC, Torrance, CA (US)

(72) Inventors: Manal Beshay, Rancho Palos Verdes, CA (US); Morgan Hatch, Long Beach, CA (US)

(73) Assignee: Intelligent Optical Systems, Inc., Torrance, CA (US)

( * ) Notice: Subject to any disclaimer, the term of this patent is extended or adjusted under 35 U.S.C. 154(b) by 595 days.

(21) Appl. No.: 15/078,519

(22) Filed: Mar. 23, 2016

Related U.S. Application Data

(60) Provisional application No. 62/136,929, filed on Mar. 23, 2015.

(51) Int. Cl.
*G01N 33/68* (2006.01)
*G01N 21/64* (2006.01)

(52) U.S. Cl.
CPC ..... *G01N 33/6893* (2013.01); *G01N 21/6428* (2013.01); *G01N 2333/47* (2013.01); *G01N 2333/78* (2013.01); *G01N 2333/916* (2013.01); *G01N 2800/108* (2013.01)

(58) Field of Classification Search
CPC .......................... G01N 33/558; G01N 33/582
See application file for complete search history.

(56) References Cited

U.S. PATENT DOCUMENTS

| | | | |
|---|---|---|---|
| 4,703,017 A | 10/1987 | Campbell et al. | |
| 5,468,648 A | 11/1995 | Chandler | |
| 5,620,861 A | 4/1997 | Cerelli et al. | |
| 5,681,707 A | 10/1997 | Hosoda et al. | |
| 6,143,506 A * | 11/2000 | Golub | G01N 33/573 435/23 |
| 6,210,978 B1 | 4/2001 | Hatch et al. | |
| 6,485,982 B1 | 11/2002 | Charlton | |
| 2001/0055751 A1* | 12/2001 | Reiter | A61K 39/395 435/4 |

(Continued)

FOREIGN PATENT DOCUMENTS

| | | |
|---|---|---|
| EP | 0212455 B1 | 10/1990 |
| WO | 1990009587 A1 | 8/1990 |
| WO | 1995012124 A1 | 5/1995 |

OTHER PUBLICATIONS

Gideon A. Rodan, Introduction to Bone Biology, Bone, 13, 1992, pp. S3-S6.

(Continued)

*Primary Examiner* — Rebecca L Martinez
(74) *Attorney, Agent, or Firm* — Brian Billett

(57) ABSTRACT

Disclosed are embodiments of a lateral flow test strip (LFTS) platform which measure osteocalcin (OC) and deoxypyridinoline (Dpd) in saliva to identify early indications of bone loss and minimize bone fracture risk associated with osteoporosis. The OC assay embodiments are based on the experimentally identified optimal markers which exhibit selectivity with very low false positives, and sensitivity relevant to clinical requirements. A prospective clinical study sampling of 20 patients demonstrated excellent correlation of OC in saliva with bone mineral density (BMD). Salivary OC and Dpd levels were validated with a standard commercial ELISA kit against serum (OC) and urine (Dpd).

2 Claims, 9 Drawing Sheets

(56) References Cited

U.S. PATENT DOCUMENTS

| | | | |
|---|---|---|---|
| 2004/0082018 A1* | 4/2004 | Ekema | G01N 33/5008 435/7.21 |
| 2004/0259167 A1* | 12/2004 | Hellman | C07K 14/78 435/7.1 |
| 2006/0253262 A1* | 11/2006 | Ching | C12Q 1/6883 702/20 |
| 2006/0263825 A1* | 11/2006 | Denny | G01N 33/5091 435/7.1 |
| 2008/0260820 A1* | 10/2008 | Borrelly | A61K 9/0019 424/463 |
| 2009/0246795 A1 | 10/2009 | Hayashi et al. | |
| 2011/0274729 A1* | 11/2011 | Collins | A61L 27/34 424/400 |
| 2012/0276193 A1* | 11/2012 | Graversen | C07K 16/2896 424/450 |
| 2014/0057362 A1 | 2/2014 | Markovsky et al. | |
| 2014/0341888 A1* | 11/2014 | Weeks | C07K 16/244 424/133.1 |

OTHER PUBLICATIONS

Kaisa K. Ivaska et. al, Urinary Osteocalcin as a Marker of Bone Metabolism, Clinical Chemistry, 51, 2005, pp. 618-628.

Patrick Garneo et. al, Biochemical markers of bone turnover: Applications for Osteoporosis, Endocrinology and Metabolism Clinics of North America, vol. 27 Issue 2, 1998, pp. 303-323.

John W. McGehee, Jr. et. al, Biomarkers of bone turnover can be assayed from human saliva, Journal of Gerontology, vol. 59A, No. 3, 2004, pp. 196-200.

Nelson B. Watts, Clinical utility of biochemical markers of bone remodeling, Clinical Chemistry, 45:8(B), 1999, pp. 1359-1368.

Markus J. Seibel, Clinical application biochemical markers of bone turnover, Arq Bras Endocrinol Metab, 50(4), 2006 pp. 603-620.

* cited by examiner

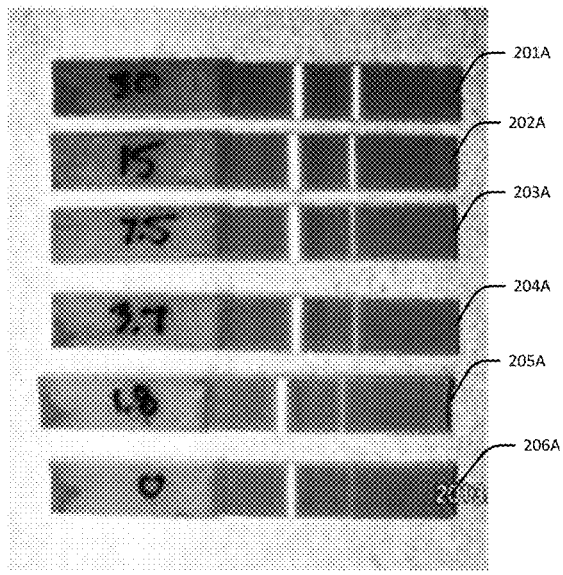
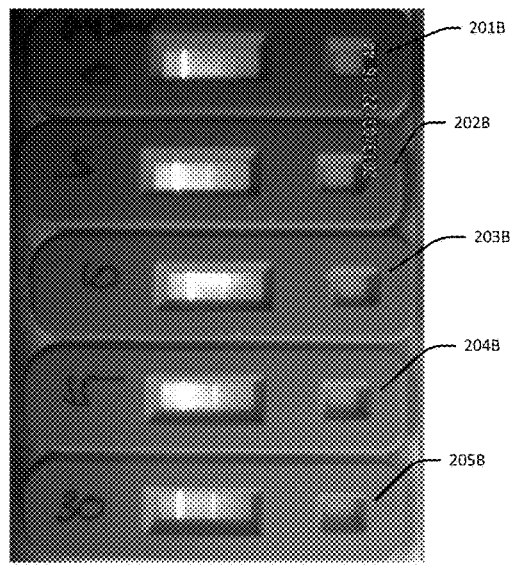
Figure 2A
Figure 2B

| Test Result | Non-Osteoporotic (BMD ≥ 120) | Osteoporotic (BMD < 120) |
|---|---|---|
| - Test (OC ≥ 10) | 4 (44%) | 0 (0%) |
| + Test (OC < 10) | 5 (56%) | 8 (100%) |
| Total | 9 (100%) | 8 (100%) |

| Membrane Striped Capture Ab Clone # | Latex Conjugated Antibodies [0.5mg/mL] | | | | | | | | | | | |
|---|---|---|---|---|---|---|---|---|---|---|---|---|
| | 939 | | 849 | | H10 | | 11F8 | | 3G8 | | 2H9 | |
| | Synthetic | Native | Synthetic | Native | Synthetic | Native | Synthetic | Native | Synthetic | Native | Synthetic | Native |
| Fitzgerald 939 | No | No | No | No | No | Yes-weak | No | No | No | No | No | No |
| Fitzgerald 940 | Yes | No | No | No | Yes | No | No | No | Yes | No | No | No |
| Novus Biological H10 | No | No | No | No | No | No | No | No | No | No | No | No |
| Novus Biological 11F8 | Yes | No | No | No | No | No | No | No | Yes | No | No | No |
| Thermo 849 | No | No | No | No | No | No | No | No | No | No | No | No |
| Thermo 3G8 | No | No | No | No | No | No | No | No | No | No | No | No |
| Hytest 2H9 | Yes | No | No | No | Yes-weak | No | No | No | Yes | No | No | No |

Figure 8

| Resorption | Formation |
|---|---|
| Urinary calcium | Bone-specific alkaline phosphatase |
| Tartrate resistant acid phosphatase | Osteocalcin |
| Bone sialoprotein | Pro-collagen I extension peptides |
| Cross-links (pyridinoline, deoxypyridinoline, N-telopeptide, C-telopeptide, C-terminal telopeptide of type I collagen) | Carboxy terminal (PICP)<br>Amino terminal (PINP) |

Figure 9

SYSTEM AND METHOD FOR BONE LOSS ASSAY

RELATED APPLICATIONS

This application for patent claims the benefit of provisional application 62/136,929 filed on Mar. 23, 2015. The application is incorporated herein in its entirety.

GOVERNMENT LICENSE RIGHTS

This invention was made with government support under contract #41R43DE022478-01 awarded by the National Institute of Health. The government has certain rights in the invention.

FIELD OF THE INVENTION

This field of this disclosure relates generally to the assay of biological markers for bone loss.

BACKGROUND

Bone health is regulated in a tightly coupled metabolic process between bone formation (by osteoblasts) and bone resorption (by osteoclasts). In healthy bone these processes are in balance; however, these rates may become uncoupled due to diseases affecting this regulation (Paget's disease, metastatic bone cancer), or hormonal changes, as in post-menopausal women. When bone resorption occurs more than bone formation, a net loss in bone mineral density (BMD) results, which can lead to diseases such as osteoporosis. The traditional approach to measuring BMD is dual energy X-ray absorption (DEXA), reported as a T-score (standard deviation from mean BMD) or Z-score (standard deviation from age-matched BMD). However, DEXA is an expensive procedure, and is not readily available for general population screening. The development of a viable screening diagnostic exam for early detection of BMD loss is a long standing problem.

SUMMARY OF THE INVENTION

Disclosed is a system for screening is the detection of biomarkers of bone formation and degradation, which can be assayed in human serum or urine via concentrations of osteocalcin (OC) and deoxypyridinoline (Dpd), respectively. Various embodiments of diagnostic systems disclosed reliably identify the concentrations of these biomarkers in human saliva which provides clinicians an opportunity to improve the diagnosis and prevention of osteoporosis, as well as provide a noninvasive method for convenient population screening.

Disclosed are embodiments of a lateral flow test strip (LFTS) platform which measure osteocalcin (OC) and deoxypyridinoline (Dpd) in saliva to identify early indications of bone loss and minimize bone fracture risk associated with osteoporosis. The OC assay embodiments are based on the experimentally identified optimal markers which exhibit selectivity with very low false positives, and sensitivity relevant to clinical requirements. A prospective clinical study sampling of 20 patients demonstrated excellent correlation of OC in saliva with bone mineral density (BMD). Salivary OC and Dpd levels were validated with a standard commercial enzyme-linked immunosorbent assay (ELISA) kit against serum (OC) and urine (Dpd).

BRIEF DESCRIPTION OF THE DRAWINGS

FIG. 2A shows a photograph of sample quantified lateral flow assay (LFA) test strips with measured levels of Dpd.

FIG. 2B shows a photograph of sample quantified LFA test strips with measured levels of OC.

FIG. 8 is a chart of tested and identified optimal combinations of reagents for detecting biomarkers.

FIG. 9 is a chart of identified biomarkers suitable for various embodiments of the disclosed LFTS platform.

DETAILED DESCRIPTION

The disclosed LFTS platform is a rapid immunochromatographic assay comprised of a test strip with several membranes that house all the reagents necessary for the test. The analyte of interest is applied in the sample medium (OC or Dpd in saliva), wherein it is captured in the test in a sandwich-antibody immunocomplex coupled to fluorescent detection. Monoclonal antibodies specific for OC or Dpd are conjugated to fluorescently labeled microparticles and deposited on the conjugate pad. Upon adding the sample to the sample pad, the saliva resolubilizes the dried antibody conjugates and forms an analyte-antibody conjugate complex, which is captured by another monoclonal antibody specific for OC or Dpd immobilized to the nitrocellulose membrane. Excitation of captured fluorescent particles generates signal response proportional to the concentration of reagent in the sample.

Figure 1:
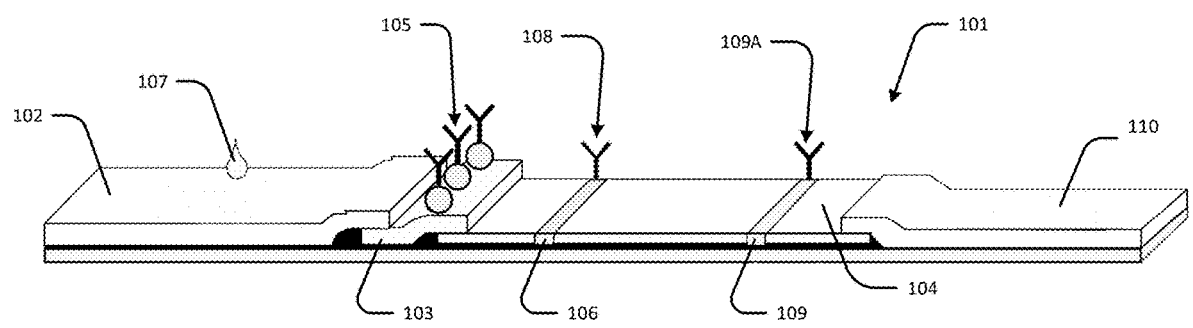
FIG. 1 shows a single biomarker lateral flow test strip.

Shown in FIG. 1 is an exemplar LFTS 101 for a single biomarker configuration. The LFTS platform includes sample pad 102, conjugate pad 103, nitrocellulose membrane 104 and wicking pad 110. Fluorescently labeled detector antibodies (OC or Dpd) 105 are deposited onto carried on the conjugate pad and capture antibodies (OC or Dpd) 108 are immobilized to the nitrocellulose membrane as the capture line 106. A control line 109 is also located on the nitrocellulose membrane. The control detector antibody 109A is immobilized on the control line 109. Flow of the sample 107 is mediated by a combination of capillary action through the membranous components from the sample pad 102 to the absorbent pad 110, and by pressure from the liquid in the sample pad pushing toward the absorbent pad.

Experimental results for determining optimal configuration of the LFTS system were conducted by the following procedure. Separate, finalized test strips for OC and Dpd were placed in plastic cassettes for testing. The cassettes have an open window to view the test results, and a sample port where the sample is applied. In this embodiment the widely-used Qiagen ESE test strip fluorescent reader was adapted and calibrated with customized optical settings of emission and excitation wavelengths to read the selected fluorescent label. Other readout devices can be used for the reported platform measurements; such as LRE/SOFIA by Quidel, Cell-phone readout by Holomics, and RDS-1500 PRO by Detekt Biomedical. Saliva samples from 20 donor patients were obtained. Collected saliva samples were kept frozen at −80° C. until tested. Frozen samples were thawed, centrifuged to remove large particulates, and diluted 1 to 1 with our running buffer. Tests were performed in triplicate with each saliva sample. After adding 100 uL of sample volume to each test, the tests flowed for 10 minutes before the results were read with the ESE reader.

Figure 3:
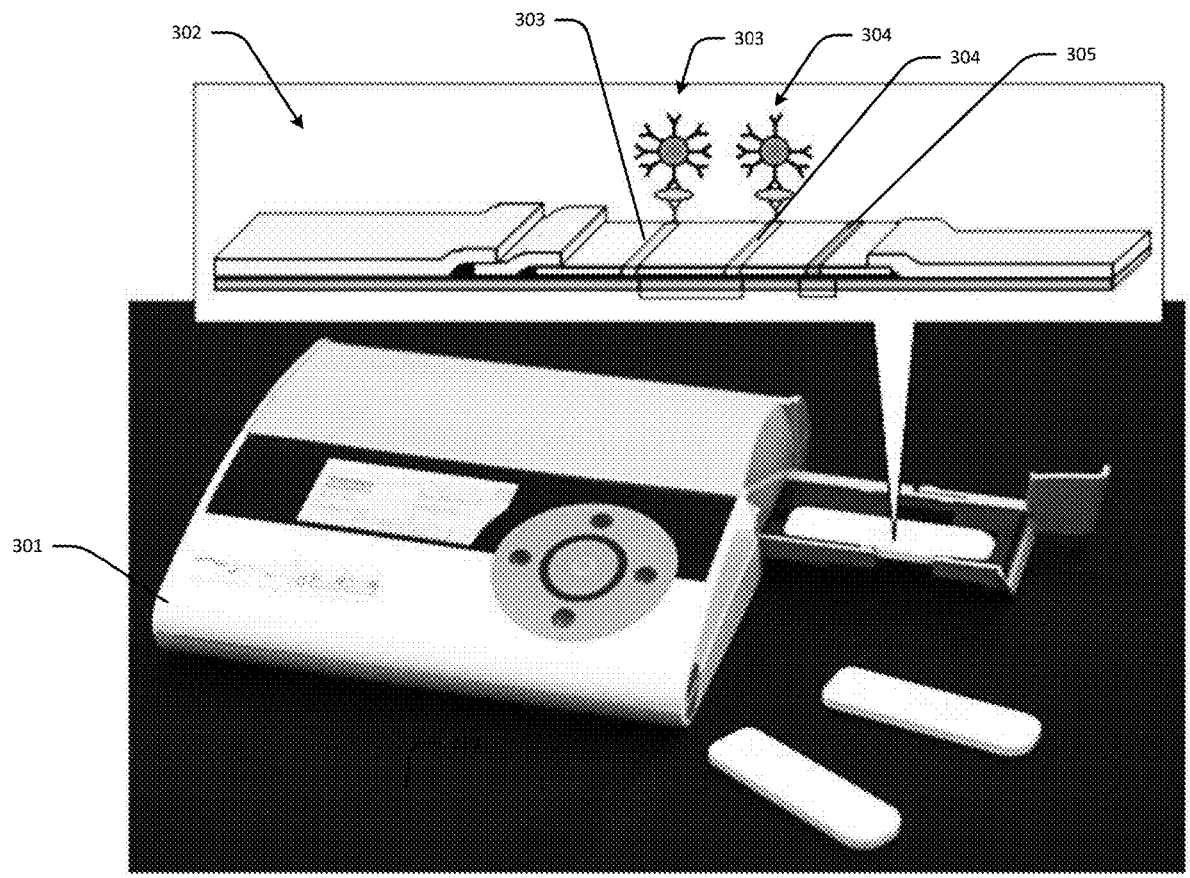
FIG. 3 shows a multiplex biomarker lateral flow test strip and test strip reader apparatus.

Shown in FIG. 2A and FIG. 2B are exemplar samples. Shown are samples with Dpd concentrations of 30 nmol/L 201A, 15 nmol/L 202A, 7.5 nmol/L 203A, 3.7 nmol/L 204A, 1.8 nmol/L 205A and 0 nmol/L 206A. Formation of sandwich antibody detection with decreasing concentrations of Dpd. Fluorescence was observed under an ultra-violet (UV) light source. Shown in FIG. 2B are exemplar OC samples with intensity observed from spiking synthetic OC in saliva. Shown tests were run in cassettes. Fluorescence was observed under UV light source for the samples 0 ng/mL 201B, 5 ng/mL 202B, 10 ng/mL 203B, 15 ng/mL 204B and 30 ng/mL 205B Shown in FIG. 3 is the fluorescent reader apparatus 301 utilized for single and multiplex test strips. Shown in the inset is an embodiment for a multiplex LFTS 302 with multiple detection lines (multiplex) 303 and 304 and control line 305.

A standard commercial enzyme-linked immunosorbent assay (ELISA) test kit was used to validate the embodiment LFTS platform with patient saliva samples. A correlation value of 0.85 was obtained with OC.

In various embodiments salivary OC and Dpd concentrations are correlated with serum (OC) and urinary (Dpd) levels from the same patient using ELISA measurements. Samples are normalized by protein concentration to adjust for salivary specific gravity. The resulting high correlation confirms the reliability of salivary markers for the disclosed embodiment.

Figure 4:
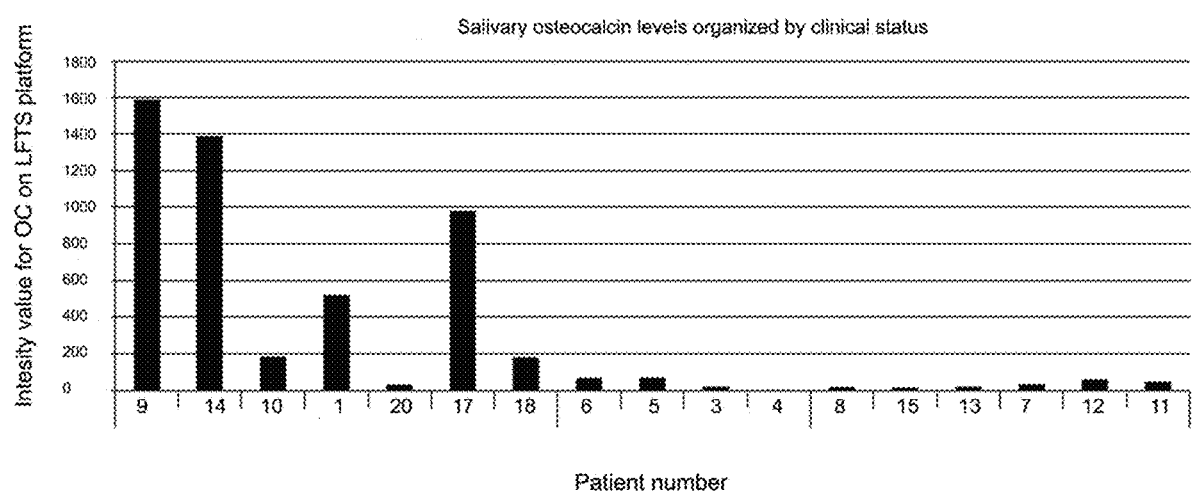
FIG. 4 shows a chart of clinical patient results for testing salivary OC.

Shown in FIG. 4 are results for patient samples categorized into three main groups—normal, osteopenic, and osteoporotic—showed high amounts of OC in normal patients, and low OC in osteopenic/osteoporotic patients.

Note that for purposes of testing various embodiments, after adding 100 uL of sample volume to each test, the tests flowed for 10 minutes before the results were read with the ESE reader.

To determine the optimum LFA components, incremental assay optimization steps were carried out for both OC and DPD assays, including capture antibody concentration, assay running buffers, purification of the antibody reagents, addition of surfactants, selection of LFA membranes, conjugate pad selection, and fabrication/drying protocols.

FIG. 8 shows a chart of tested capture and detector reagents along with those combinations which proved to be effective for the disclosed embodiment. To identify the antibody pair with the best affinity to osteocalcin (OC), OC reagents were screened from Fitzgerald, Novus Biologicals, Thermo Scientific, and Hytest that includes mouse anti-OC monoclonal and rabbit polyclonal antibodies for sandwich pairing and antigen testing. The following pairs were the only combinations that bound synthetic osteocalcin as membrane/detector: 940/939, 11F8/939, 2H9/939, 940/H10, 2H9/H10, 940/3G8, 11F8/3G8, 2H9/3G8. Two pairs bound strongly with native osteocalcin as membrane/detector: 940/H10, and 2H9/H10, and were used for further assay optimization and testing. Mouse monoclonal antibodies against DPD were acquired from Quidel and screened along with an antibody from a human DPD ELISA kit (MyBioSource).

Figure 5A:
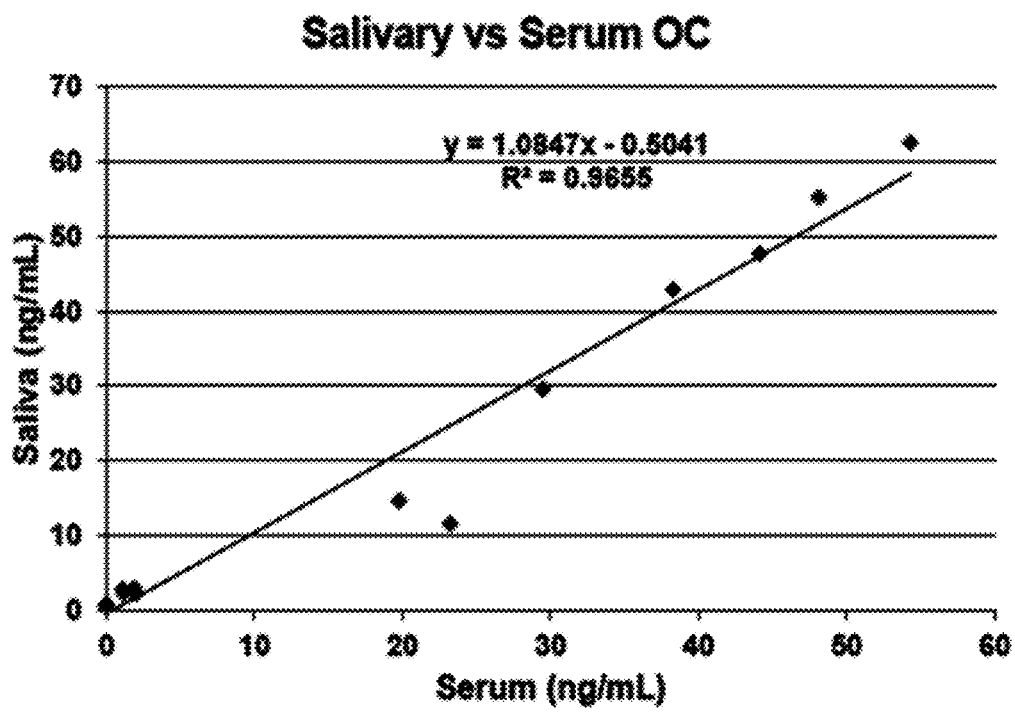
FIG. 5A shows a chart of measured salivary OC compared against measured OC from serum.
Figure 5B:
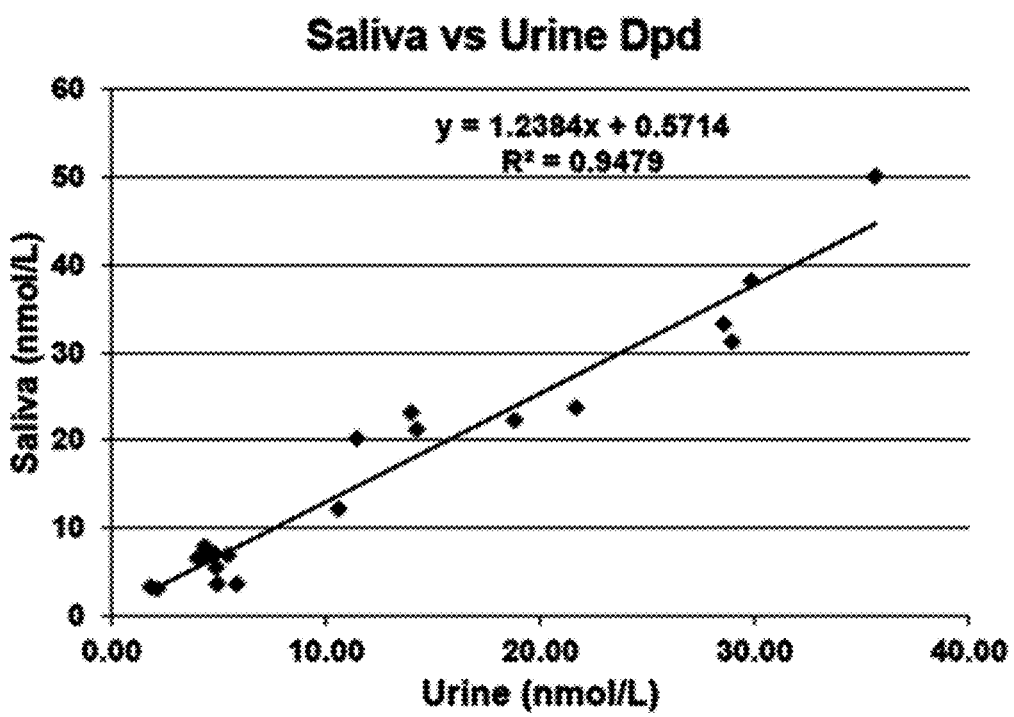
FIG. 5B shows a chart of measured salivary Dpd compared against measured Dpd from urine.

Salivary OC and Dpd concentrations were correlated with serum (OC) and urinary (Dpd) levels from the same patient using ELISA measurements. Samples were normalized by protein concentration to adjust for salivary specific gravity. The resulting high correlation suggested the reliability of salivary markers. Shown in FIG. 5A are results for salivary experimental measurements vs. the serum OC validation marker. Shown in FIG. 5B are results for salivary experimental measurements vs. the urine Dpd validation marker.

Figure 6:
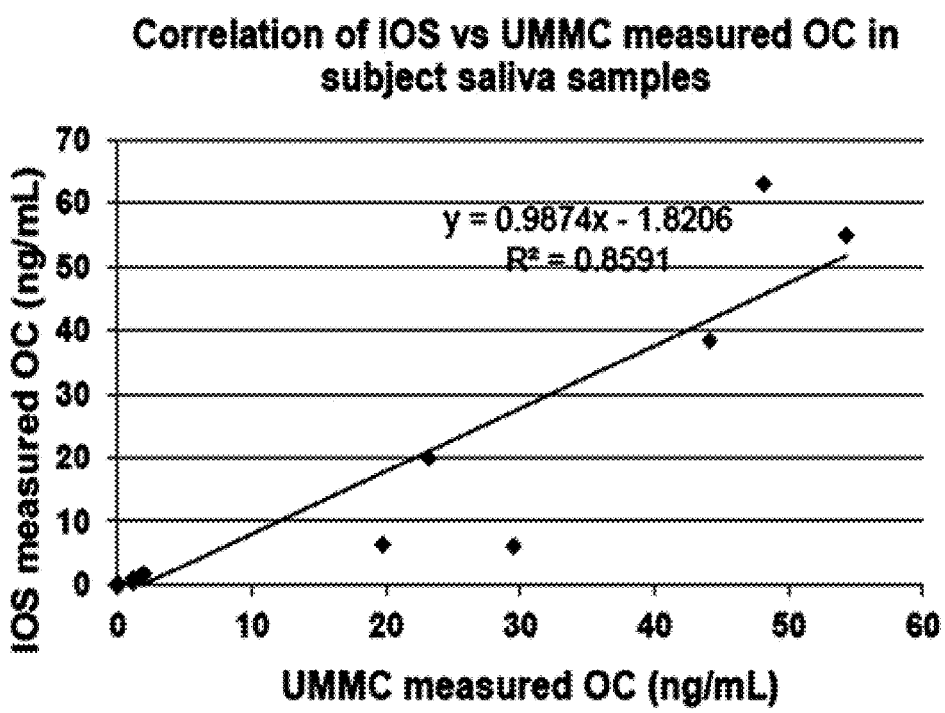
FIG. 6 shows a correlation computation for the embodiment measured OC against the laboratory ELISA measured OC.
Figures 7A, 7B:
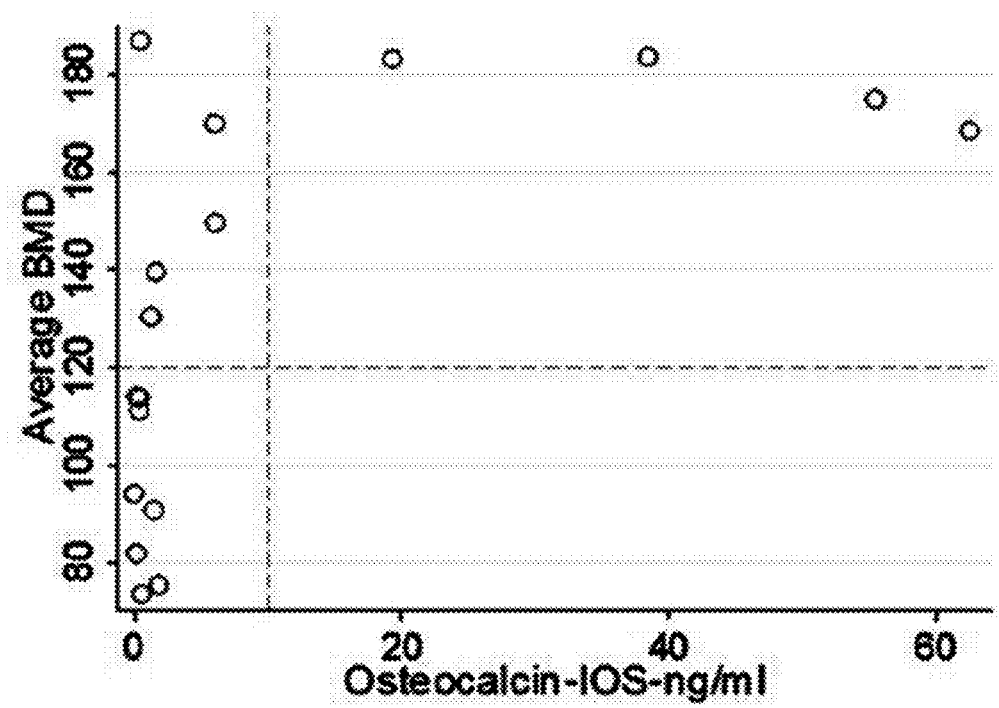
FIG. 7A shows a chart of LFTS measured OC compared with BMD levels in subjects.
FIG. 7B shows a detailed graph comparing levels of subject BMD and measured OC from the developed embodiment LFTS.

A standard commercial ELISA test kit was used to validate the disclosed LFTS platform with patient saliva samples. A correlation value of 0.85 was obtained with OC. FIG. 6 shows the correlation of OC measurements.

In various embodiments, the disclosed quantifiable LFTS may contain multiplexed biomarkers for both OC and Dpd. The LFTS shown in FIG. 3 illustrates a multiplexed LFA.

In various embodiments, additional biomarkers are utilized in the disclosed LFTS in either the disclosed single or multiplexed quantifiable methodology. Bone turnover biomarkers are represented in compounds such as collagen precursors, enzymes, and by-products, or degradation products involved with the bone formation (osteoblast) and bone resorption (osteoclast) processes. In various embodiments, one or more of these biomarkers are utilized in the disclosed LFTS for optimal or additional accuracy for screening examination. FIG. 9 provides a chart of the biomarkers identified for use in these embodiments.

The disclosed sensitive lateral flow assay-based technique are capable of the detecting bone formation marker osteocalcin in saliva at clinically relevant levels which has been demonstrated and correlated to BMD, utilizing the disclosed readout system which as disclosed is easily integrated in a single platform for point-of-care (POC) applications.

Other embodiments of the invention utilize equivalent monoclonal antibody capture and detector reagents and reagent pairs for the assay.

What has been described herein is considered merely illustrative of the principles of this invention. Accordingly, it is well within the purview of one skilled in the art to provide other and different embodiments within the spirit and scope of the invention.

What is claimed is:

1. A method for screening for osteoporosis comprising:
   a. obtaining a saliva sample from a subject;
   b. applying the saliva sample to a lateral flow test strip, wherein the strip comprises a conjugate pad deposited with a fluorescently labeled detector antibody, and at least one capture line reactive to osteocalcin;
   c. placing the test strip in a fluorescent reader calibrated to quantitatively measure osteocalcin concentration at a given sample volume;
   d. performing a screening diagnostic evaluation according to a quantitative measurement obtained from the reader;
   wherein the at least one capture line comprises a capture antibody specific to osteocalcin, and a control line; wherein the capture antibody and the fluorescently labeled detector antibody pair are chosen from the group consisting of:
   a. 940/939,
   b. 11F8/939,
   c. 2H9/939,
   d. 940/H10, e. 2H9/H10,
f. 940/3G8,
g. 11F8/3G8.

2. The method for screening for osteoporosis as in claim 1, wherein the conjugate pad fluorescent reagent is a labeled detector antibody conjugated to fluorescent microparticles which is paired with a capture antibody immobilized on the membrane on one of the at least one capture line.

* * * * *